United States Patent
Warshavski (10) Patent No.: US 10,989,653 B2
(45) Date of Patent: Apr. 27, 2021

(54) COLOR IMAGING BY DISCRETE NARROW-BAND SYNCHRONIZED ILLUMINATION

(71) Applicant: Omri Warshavski, M.P Misgav (IL)

(72) Inventor: Omri Warshavski, M.P Misgav (IL)

(73) Assignee: Omri Warshavski, M.P Misgav (IL)

( * ) Notice: Subject to any disclaimer, the term of this patent is extended or adjusted under 35 U.S.C. 154(b) by 76 days.

(21) Appl. No.: 16/313,167

(22) PCT Filed: Jun. 27, 2017

(86) PCT No.: PCT/IL2017/050715
§ 371 (c)(1),
(2) Date: Dec. 26, 2018

(87) PCT Pub. No.: WO2018/002923
PCT Pub. Date: Jan. 4, 2018

(65) Prior Publication Data
US 2019/0154569 A1      May 23, 2019

Related U.S. Application Data

(60) Provisional application No. 62/354,821, filed on Jun. 27, 2016.

(51) Int. Cl.
*G06K 9/00* (2006.01)
*G01N 21/31* (2006.01)
(Continued)

(52) U.S. Cl.
CPC ........... *G01N 21/31* (2013.01); *A61B 5/0059* (2013.01); *G01J 3/0218* (2013.01); *G01J 3/46* (2013.01);
(Continued)

(58) Field of Classification Search
None
See application file for complete search history.

(56) References Cited

U.S. PATENT DOCUMENTS 9,320,428 B2    4/2016  Taylor
2002/0001080 A1  1/2002  Miller
(Continued)

FOREIGN PATENT DOCUMENTS

FR       2731086 A1    8/1996
JP       2016032494     3/2016
KR     1020160064021    6/2016
RU       2308116 C1    10/2007

*Primary Examiner* — Hadi Akhavannik
(74) *Attorney, Agent, or Firm* — Soroker Agmon Nordman (57) ABSTRACT

A color imaging system and method, the method comprising, for a plurality of predetermined wavelength bands of illumination, calculating weight coefficients representing the contribution of each of the wavelength bands to a specific color space, individually controlling illumination intervals of each of a plurality of illumination sources, wherein each of the illumination sources is configured to provide illumination via a waveguide in a different predetermined narrow band of wavelengths, controlling an image sensor to capture a set of monochromatic image frames synchronously with the illumination intervals, receiving a set of the captured monochromatic image frames, and generating color image data by calculating a combination of the set of image frames, each weighted by the corresponding coefficient.

12 Claims, 4 Drawing Sheets

(51) Int. Cl.
*G01N 21/25* (2006.01)
*G01N 21/47* (2006.01)
*G01J 3/50* (2006.01)
*G01J 3/02* (2006.01)
*A61B 5/00* (2006.01)
*G01J 3/46* (2006.01)
*G01N 21/64* (2006.01)

(52) U.S. Cl.
CPC ............ *G01J 3/501* (2013.01); *G01N 21/251* (2013.01); *G01N 21/474* (2013.01); *G01N 21/6408* (2013.01); *G01N 2021/479* (2013.01); *G01N 2021/4742* (2013.01); *G01N 2201/0627* (2013.01); *G01N 2201/0826* (2013.01)

(56) References Cited

U.S. PATENT DOCUMENTS

| | | |
|---|---|---|
| 2005/0065406 A1 | 3/2005 | Cline et al. |
| 2006/0146326 A1* | 7/2006 | Nagashima ............... G01J 3/46 356/328 |
| 2007/0179366 A1 | 8/2007 | Pewzner et al. |
| 2007/0199998 A1* | 8/2007 | Kotlarsky ........... G06K 7/10801 235/462.45 |
| 2010/0079581 A1 | 4/2010 | Russell et al. |
| 2014/0193050 A1* | 7/2014 | Miller ....................... G06T 5/50 382/128 |
| 2014/0270440 A1* | 9/2014 | Inglese ................. A61B 6/5205 382/131 |
| 2014/0316284 A1 | 10/2014 | Rege et al. |

* cited by examiner

COLOR IMAGING BY DISCRETE NARROW-BAND SYNCHRONIZED ILLUMINATION

FIELD OF THE INVENTION

The present disclosure generally relates to methods for obtaining information about dark hollow environments, and more specifically to endoscopy and robotic surgery.

BACKGROUND

Color images are commonly captured using natural broadband light ("white light") and a set of three filters applied over the imaging sensor. A color image usually contains three different color layers (Red, Green, and Blue) mimicking the spectral sensitivities of the human eye cone cell. The different color layers are combined to create a color image were each pixel in color image is represented by those three values or one of their derivatives. Some known endoscopy methods use a light source and a plurality of filters for separation of colors, thus losing a major portion of the light intensity. This requires extended exposure time of the image sensors and/or utilization of very strong and cumbersome illumination sources in the input of the endoscope.

Additionally, some imaging methods aim to record spectral information, for example multi spectral or hyper spectral information, and/or use a large amount of spectral channels for generation of a high quality color image. Some methods use large sets of images of a known spectrum to estimate the reflectance spectra out of color images in order to enhance hard to see features in the image.

SUMMARY

According to an aspect of some embodiments of the present invention, there is provided a color imaging method including, for a plurality of predetermined wavelength bands of illumination, calculating weight coefficients representing the contribution of each of the wavelength bands to a specific color space, individually controlling illumination intervals of each of a plurality of illumination sources, wherein each of the illumination sources is configured to provide illumination via a waveguide in a different predetermined narrow band of wavelengths, controlling an image sensor to capture a set of monochromatic image frames synchronously with the illumination intervals, receiving a set of the captured monochromatic image frames, and generating color image data by calculating a combination of the set of image frames, each weighted by the corresponding coefficient.

Optionally, the method includes controlling exposure times of the monochromatic image sensor synchronously with illumination transmitted via at least one of the illumination sources.

Optionally, the method includes operating the illumination sources according to one or more pre-programmed operation protocol of illumination.

Optionally, the illumination protocol comprises multiple illumination intervals, wherein in each illumination interval another illumination source of another respective illumination wavelength band is operated.

Optionally, the illumination protocol comprises multiple illumination intervals, wherein at least two of the illumination intervals have different durations.

Optionally, the illumination protocol comprises multiple illumination intervals, wherein a certain illumination band is operated in more than one illumination interval.

Optionally, the illumination protocol comprises multiple illumination intervals, wherein more than one illumination band are operated simultaneously during at least one illumination interval.

Optionally, the method includes detecting a base illumination level by controlling the illumination sources to provide no illumination during a certain interval and capturing image data by the image sensor when no illumination is provided by the sources, and calibrating the image sensor and/or generated color image based on the detected base illumination level.

Optionally, the method includes extracting from the received frames information about at least one of a list consisting of: fluorescence, auto-fluorescence, speckle patterns and structured light.

Optionally, the method includes illumination in wavelengths which are outside the human visible range but are still in the sensing range of the image sensor.

Optionally, the method includes extracting information from coherence of sensed reflected light included in the received frames.

Optionally, the method includes extraction of depth information from deformation of a structured light pattern.

Optionally, the method includes extraction of the temporal changes in the standard deviation of the image intensity in speckle patterns identified in some of the captured light bands, while a coherent illumination is applied during the illumination interval.

According to an aspect of some embodiments Or the present invention, there is provided a color imaging system including a plurality of illumination sources, each configured to provide illumination via a waveguide in a different predetermined narrow band of wavelengths, and a processor configured to execute code, the code comprising instructions for individually controlling illumination intervals of each of the plurality of illumination sources, controlling an image sensor to capture a set of monochromatic image frames synchronously with the illumination intervals, receiving a set of the captured monochromatic image frames, and generating color image data from the received captured image frames.

Optionally, the system includes a sensing module comprising: one or more waveguides configured to transmit illumination from the different illumination sources, respectively, and a monochromatic image sensor.

Optionally, the processor is configured to operate the illumination sources according to a pre-programmed operation protocol of illumination.

Optionally, the processor is configured to operate the illumination sources according to a dynamically controlled operation protocol of illumination.

Optionally, the illumination protocol comprises multiple illumination intervals, wherein in each illumination interval another illumination source of another respective illumination wavelength band is operated.

Optionally, the illumination protocol comprises multiple illumination intervals, wherein at least two of the illumination intervals have different durations.

Optionally, the illumination protocol comprises multiple illumination intervals, wherein a certain illumination band is operated in more than one illumination interval.

Optionally, the illumination protocol comprises multiple illumination intervals, wherein more than one illumination band is operated during at least one illumination interval.

Optionally, the processor is configured to detect a base illumination level by controlling the illumination sources to provide no illumination during a certain interval and capturing image data by the image sensor when no illumination is provided by the sources, and to calibrate the image sensor and/or the generated color image based on the detected base illumination level.

Optionally, processor is configured to extract from the received frames information about at least one of a list consisting of: fluorescence, auto-fluorescence, speckle patterns and structured light.

BRIEF DESCRIPTION OF THE DRAWINGS

Some non-limiting exemplary embodiments or features of the disclosed subject matter are illustrated in the following drawings.

In the drawings.

With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Identical or duplicate or equivalent or similar structures, elements, or parts that appear in one or more drawings ate generally labeled with the same reference numeral, optionally with an additional letter or letters to distinguish between similar entities or variants of entities, and may not be repeatedly labeled and/or described. References to previously presented elements are implied without necessarily further citing the drawing or description in which they appear.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

DETAILED DESCRIPTION

Some embodiments of the present, invention provide a system, and method for color imaging of dark, non-illuminated environments where there is no spatial light, for example inside a human body and/or another closed hollow space.

Some exemplary embodiments of the present invention are applicable in gastrointestinal endoscopy and/or in imaging of any other interior body lumen. However, the invention is not limited in this respect and may have other suitable applications.

There are imaging methods that enable a limited efficiency of capturing and transmission of information, for example due to the use of filters for separation of colors and/or the use of a large amount of color channels for generation of a high quality color image. As mentioned above, some imaging methods aim to record spectral information, for example multi spectral or hyper spectral information. However, in order to capture the spectral information, these methods are forced to lose imaging information, for example spatial or temporal imaging dimensions. Additionally, such methods usually provide image and/or other data with a low frame rate and/or degraded spatial resolution, making them unsuitable for real-time applications, and/or may require examination of a specific region at a time or alternately scanning of the field of view by the image sensor.

Some embodiments of the present invention solve the efficiency problem and provide enhanced information content captured in dark environments by the imaging device while simultaneously presenting a high fidelity color image, with low latency, and high resolution. The solution includes a monochromatic image sensor that captures images in synchronization with illumination intervals of various spectral bands, with no color filters involved. In some embodiments, monochromatic images are captured while illuminating in each of a set of predefined distinct spectral bands, in a different interval for each spectral band. Additionally, some of the captured spectral data is used, in some embodiments, for obtaining additional information content from reflectance spectrum of objects, for example information which is not expressed in the conventional color space Red, Green and Blue (RGB) image.

Some embodiments of the present invention may include a system, a method, and/or a computer program product. The computer program product may include a tangible non transitory computer readable storage medium (or media) having computer readable program instructions thereon for causing a processor to carry out aspects of the present invention. Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including any object oriented programming language and/or conventional procedural programming languages.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
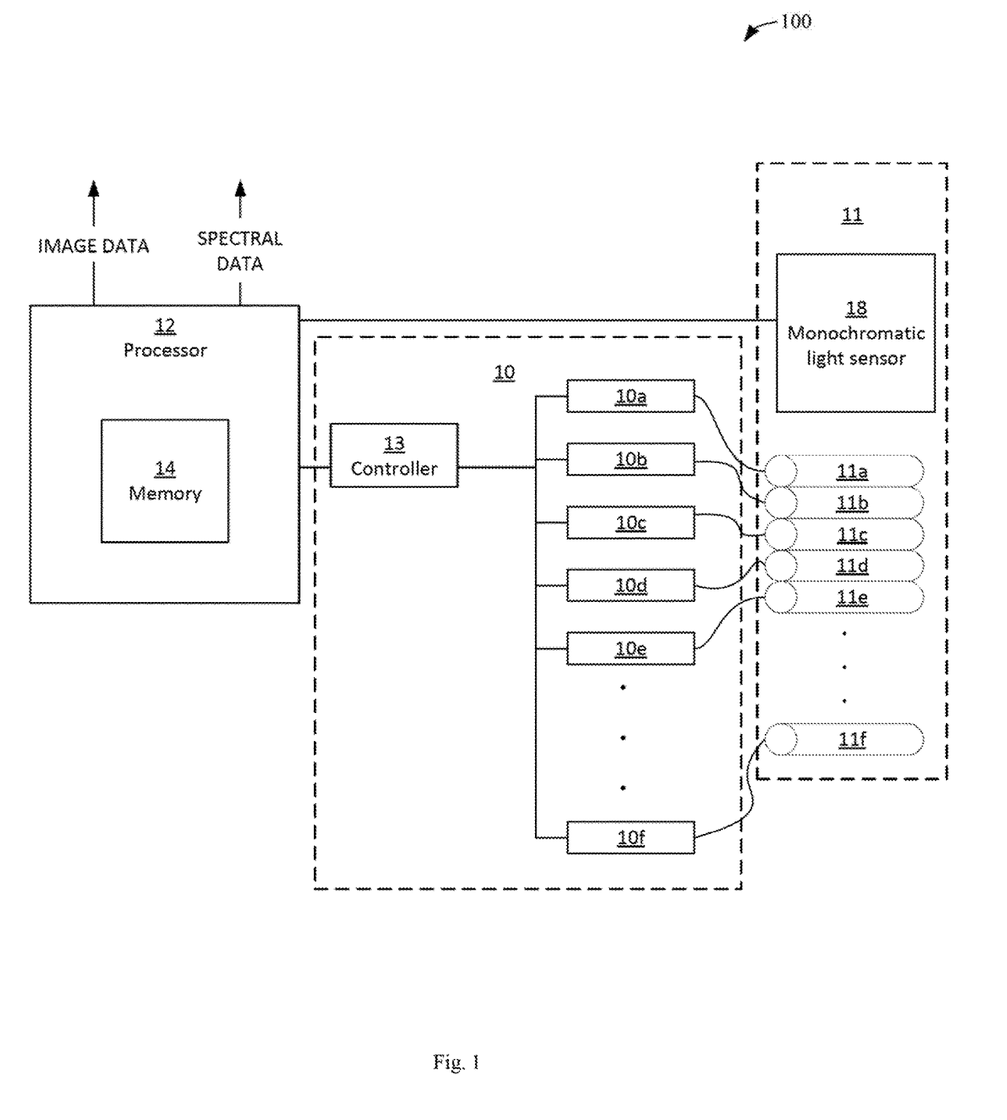
FIG. 1 is a schematic illustration of a color imaging system, according to some embodiments of the present invention.

Reference is now made to FIG. 1, which is a schematic illustration of a color imaging system 100, according to some embodiments of the present invention. System 100 may include an illumination module 10, a sensing module 11, such as an endoscope, and at least one hardware processor 12. Processor 12 may include and/or communicate with a hardware non-transitory memory 14. Memory 14 may store code instructions executable by processor 12. In some embodiments, executing the stored instructions causes processor 12 to carry out the methods described herein.

Illumination module 10 may include a controller 13 and a plurality of illumination sources, for example illumination sources 10a-10f. The invention is not limited to any specific number of illumination sources. In some embodiments, the number of illumination sources is between 4 and 50. Controller 13 may receive instructions from processor 12 and/or operate by executing a set of code instructions stored in controller 13 and/or in memory 14. Controller 13 may control illumination sources 10a-10f separately, for example to illuminate in different spectral bands in respective different intervals, for example according to a pre-defined illumination pattern. In some embodiments, controller 13 may be configured to illuminate in each interval with a combination of one or more sources, each controlled to illuminate for a certain period and/or at a certain intensity.

Illumination sources 10a-10f may each provide illumination in a different narrow band of wavelengths, for example of less than 20 nanometer (nm) spanning over a predefined range of wavelengths. For example, the range of wavelengths is defined according to a sensitivity range of a light sensor appointed to capture light reflected from objects illuminated by sources 10a-10f. For example, the range may span from Ultra Violet A (UVA) to Near Infra-Red (NIR) light, e.g. from 300 nm to 1100 nm. Illumination sources 10a-10f may include Light Emitting Diodes (LED), lasers, laser diodes, or any other suitable narrow-band illumination source. As described in more detail herein, in some embodiments, illumination sources 10a-10f are suitable in size and shape for coupling each with a corresponding configuration of waveguides 11a-11f, respectively, of sensing module 11. For example, a waveguide may be made of glass optical fiber a few meters long and may have a width of about 10-600 micrometer. For example, seven optical fibers of a diameter of about 200 micrometer may be bundled in a hexagonal shape having a diameter of about 600 micrometer. Similarly, nineteen identical fibers in a similar hexagonal shape bundle may have a diameter of about 1 millimeter.

Sensing module 11 may include a plurality of waveguides, for example waveguides 11a-11f, and a monochromatic light sensor 18. The invention is not limited to any specific number of waveguides. For example, the number of waveguides 11a-11f may correspond to the number of illumination sources 10a-10f, wherein each illumination sources may be coupled to a respective waveguide. Waveguides 11a-11f may include, for example, optical fibers and/or any other suitable optical waveguides. In some embodiments, waveguides 11a-11f may be arranged in a bundle of waveguides or multiple bundles of waveguides to facilitate passing of the waveguides together, e.g. in parallel, into body lumens and/or other dark hollow voids.

In some exemplary embodiments, at least some of the waveguides is merged into a smaller and/or split into a larger number of waveguides in the way from sources 10a-10f to a tip of sensing module 11. For example, waveguides may be merged in order to save space at the tip of sensing module 11 and/or to simplify the operation of connecting and disconnecting the sensing module 11 and the illumination module 10. For example, waveguides may be split in order to reduce the amount of energy passing through a waveguide, or to create a plurality of illumination sources at different locations at a tip of sensing module 11.

Monochromatic sensor 18 may include, for example, a Charged Coupled Device (CCD), a Complementary Metal-Oxide-Semiconductor (CMOS), a N-type Metal-Oxide-Semiconductor (NMOS), and/or any other suitable type of image sensor. Monochromatic sensor 18 may be controlled by processor 12 and/or by controller 13 to capture a digital monochromatic image, i.e. to capture the light reflected from illuminated objects in synchronization with illumination emitted from each of light sources 10a-10f via the corresponding waveguides 11a-11f. For example, sensor 18 may include a shutter, for example electronic shutter, controllable by processor 12 and/or controller 13, configured to open and close synchronously with operation of light sources 10a-10f. For example, sensor 18 may include an electronic switch controllable by processor 12 and/or controller 13, configured to turn the sensor on and off synchronously with operation of light sources 10a-10f.

In some embodiments of the present invention, processor 12 sends synchronization signals to controller 13 to initiate an illumination protocol. In some embodiments of the present invention, controller 13 may send a synchronization signal to processor 12 and/or image sensor 18 upon activation of an illumination source, thus inducing synchronized operation of image sensor 18 in response to the received synchronization signal. In some other embodiments of the present invention, the synchronization signal may alternatively be originated by the image sensor 18 or by at least one of the illumination sources 10a-10f, thus ensuring the synchronized operation between the image sensor and the illumination intervals.

Processor 12 may operate monochromatic sensor 18, for example directly or by controller 13, in a high frame rate, for example above 80 frames per second (fps). Processor 12 may generate and/or provide instructions to controller 13 to operate light sources 10a-10f in the same rate as the frame rate of sensor 18. Based on the received instruction, for example, in each illumination interval, controller 13 operates another light source or group of light sources to illuminate via waveguides 11a-11f, while sensor 18 captures the light reflected back from illuminated objects. For example, processor 12 stores data about which illumination spectral band(s) are operated in each illumination interval, and matches between a monochromatic image captured by sensor 18 in a certain illumination interval and the data about the respective illumination spectral bands operated in the same certain illumination interval. Therefore, each monochromatic image is associated with a known illumination spectral band, i.e. a known narrow wavelength band, or several concurrent illumination spectral bands, in which it was captured.

In some embodiments of the present invention, processor 12 may operate sensor 18 and/or illumination sources 10a-10f according to a pre-programmed operation protocol of illumination and light capturing designated for a certain type of information that may be extracted from the captured images. In some embodiments, processor 12 may receive commands, for example via a user interface, and operate according to the received commands, to execute one of several pre-programmed operation protocols of illumination and capturing stored, for example, in memory 14. For example, each of the preprogrammed protocols is designated for another type of information that may be extracted from the captured images.

Figure 2A:
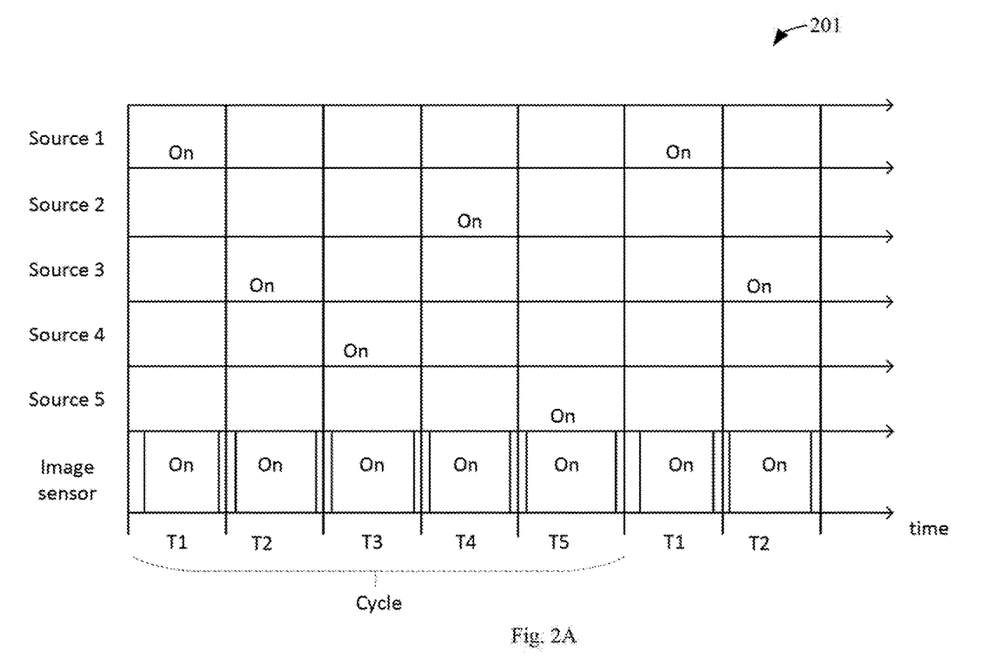
FIGS. 2A and 2B are schematic time tables illustrating exemplary operation protocols 201 and 202, respectively, according to some embodiments of the present invention.
Figure 2B:
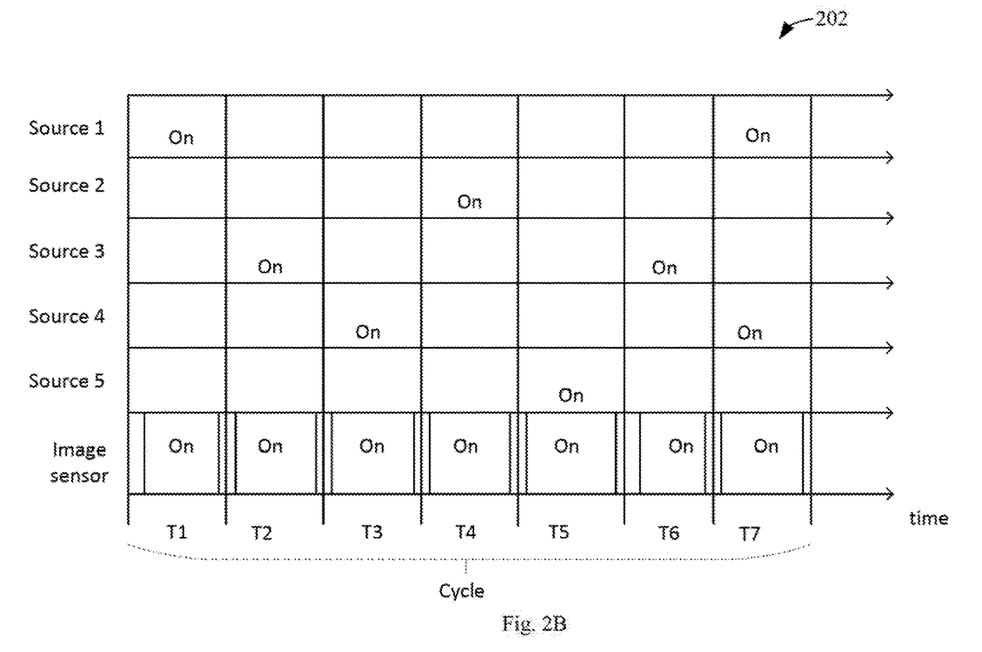

Reference is now made to FIGS. 2A and 2B, which are schematic time tables illustrating exemplary operation protocols 201 and 202, respectively, according to some embodiments of the present invention. For example, as shown in FIG. 2A, one cycle of a repetitive illumination protocol may include illumination intervals T1-T5, wherein in each interval another illumination source of another respective illumination spectral band is operated. During each of illumination intervals T1-T5, monochromatic sensor 18 captures an image by capturing reflected light within that illumination interval. In some embodiments of the present invention, illumination intervals T1-T5 and/or the capturing times within these illumination intervals may have different durations. For example, some illumination spectral bands may require longer exposure of sensor 18, for example to adapt the brightness of a certain spectral band to properties of the human eye and/or of specific equipment, such as a display device.

For example, as shown in FIG. 2B, a cycle of a repetitive illumination protocol may further include more than one illumination interval for a certain illumination spectral band. For example, an illumination source 3 may be operated in both illumination intervals T2 and T6. Additionally or alternatively, the cycle may include illumination intervals during which more than one illumination source is operated, such as illumination interval T7, for example for extraction of certain types of information.

In some embodiments of the present invention, controller 13 may control the illumination sources to provide no illumination during a certain interval, and processor 12 may detect a base illumination level by capturing image data by the image sensor when no illumination is provided by the sources. Processor 12 may calibrate the image sensor and/or the generated color image based on the detected base illumination level.

According to some embodiments of the present invention, processor 12 may calculate an RGB color image, for example a high fidelity RGB color image, by combining a set of the captured digital monochromatic images associated with respective different illumination spectral bands, in which the images are captured. In some embodiments, processor 12 calculates the RGB image and outputs the image to a display with latency of less than 100 milliseconds, for example from the time of capturing the last image in the set.

For example, processor 12 may combine the set of digital monochromatic images by allocating a weight coefficient to each illumination spectral band, so that each image is weighted according to its associated illumination spectral band or bands. For example, the coefficients are calculated by taking into account the perceived intensity by a human eye of each spectral band. For example, a spectral band perceived as less bright may be given a lower weight coefficient, so as to reflect the lower perceived luminance. In some embodiments, the coefficients are calculated according to a certain color space, such as the XYZ color space (the CIE 1931 XYZ color space) or any other suitable color space.

Figure 3:
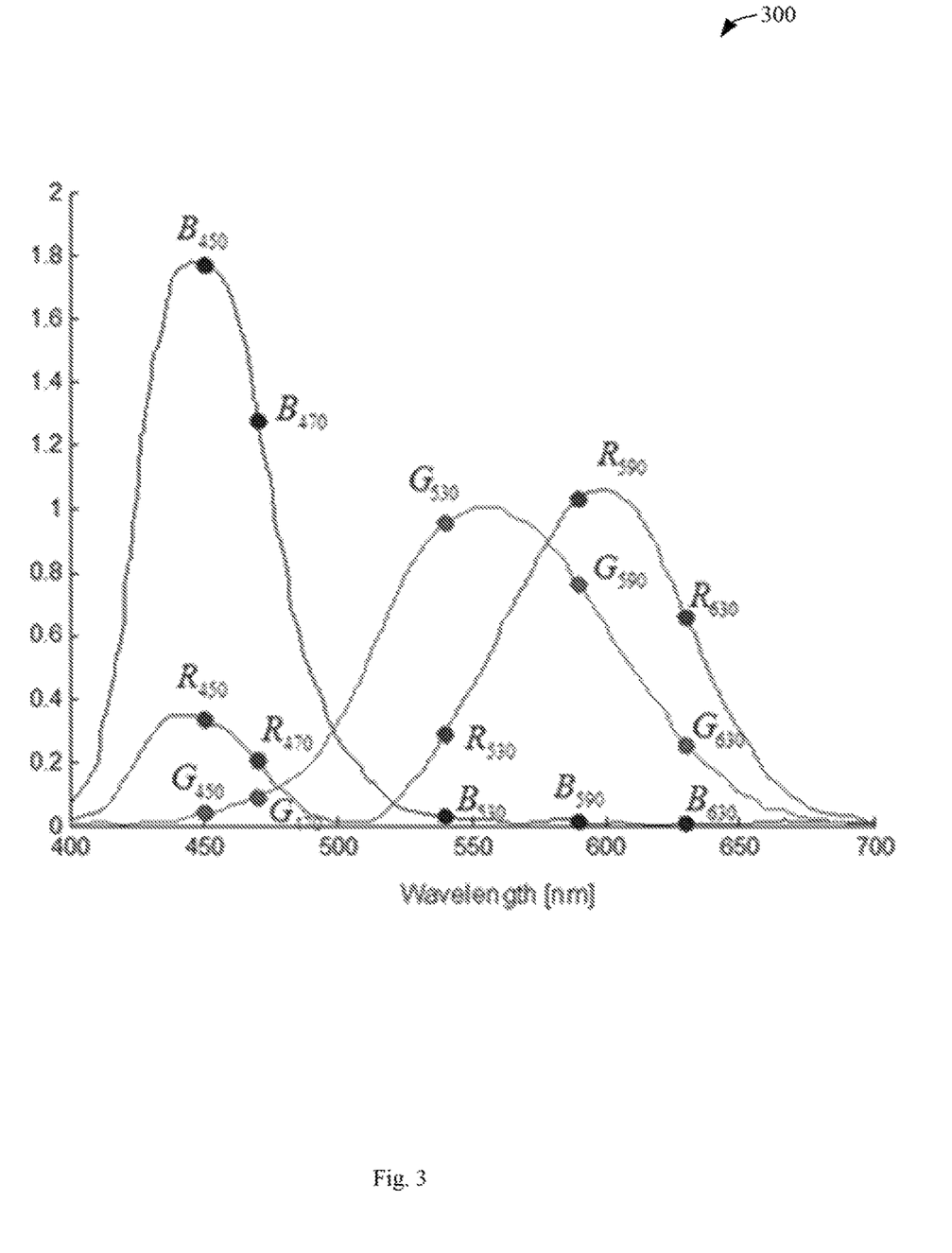
FIG. 3 is a schematic graph illustrating calculation of R, G and B coefficients based of XYZ color space, according to some embodiments of the present invention.

Reference is now made to FIG. 3, which is a schematic graph 300 illustrating calculation of R, G and B coefficients based on XYZ color space, according to some embodiments of the present invention. Graph 300 illustrates an estimation of the relative response of each of the Red, Green and Blue eye receptors to illumination of different wavelengths. For each wavelength x, the Red coefficient Rx, Green coefficient Gr and Blue coefficient Bx are Red, Green and Blue color values, determined according to the relative response of each of the Red, Green and Blue eye receptors to illumination in wavelength x, respectively. For example, as shown in FIG. 3, for illumination of 450 nm the coefficients are $R_{450}$, $G_{450}$ and $B_{450}$; for illumination of 470 nm the coefficients are $R_{470}$, $G_{470}$ and $B_{470}$; for illumination of 530 nm the coefficients are $R_{530}$, $G_{530}$ and $B_{530}$; for illumination of 590 nm the coefficients are $R_{590}$, $G_{590}$ and $B_{590}$; and for illumination of 630 nm the coefficients are $R_{630}$, $G_{630}$ and $B_{630}$. Thus, in some embodiments, the coefficients may include additional scalar factor to compensate for the non-uniform sampling between adjacent spectral bands.

Figure 4:
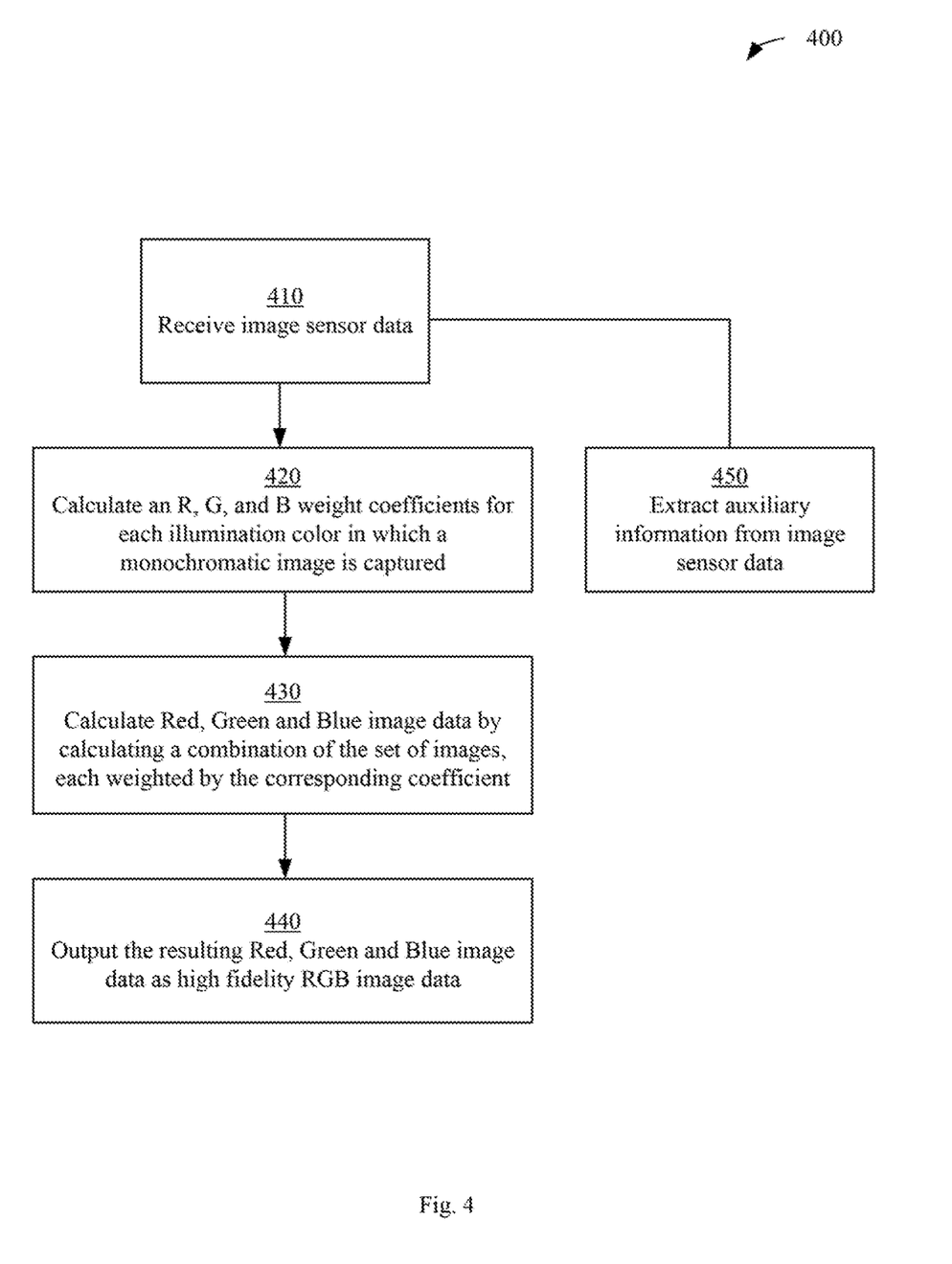
FIG. 4 is a schematic flowchart illustrating a method for calculating a high fidelity RGB color image, according to some embodiments of the present invention.

Reference is now made to FIG. 4, which is a schematic flowchart illustrating a method 400 for calculating a high fidelity RGB color image, according to some embodiments of the present invention. As indicated in block 410, processor 12 may receive data captured by image sensor 18. As indicated in block 420, for each illumination color in which a monochromatic image is captured, processor 12 may calculate an R, G, and B weight coefficients, representing the response to this illumination color of each of the Red, Green and Blue human eye color receptors, respectively.

As indicated in block 430, processor 12 may calculate Red image data by calculating a combination of the set of images, each weighted by the corresponding R coefficient, Green image data by calculating a combination of the set of images, each weighted by the corresponding G coefficient, and Blue image data by calculating a combination of the set of images, each weighted by the corresponding B coefficient. As in in block 440, processor 12 may output the resulting Red, Green and Blue image data as high fidelity RGB image data. For example, for five narrow wavelength bands of illumination centered at 450 nm, 470 nm, 530 nm, 590 nm and 630 nm. The RGB image data may be calculated according to the transformation:

$$\begin{pmatrix} R \\ G \\ B \end{pmatrix} = \begin{pmatrix} R_{450}I_{450} + R_{470}I_{470} + R_{530}I_{530} + R_{590}I_{590} + R_{630}I_{630} \\ G_{450}I_{450} + G_{470}I_{470} + G_{530}I_{530} + G_{590}I_{590} + G_{630}I_{630} \\ B_{450}I_{450} + B_{470}I_{470} + B_{530}I_{530} + B_{590}I_{590} + B_{630}I_{630} \end{pmatrix}$$

Wherein R, G and B are matrices representing the Red, Green and Blue image data and Ix is a matrix representing the monochromatic image captured during illumination at wavelength x. Thus, in some embodiments, the coefficients may include additional scalar factor to compensate for the nom-uniform sampling between adjacent spectral bands or and the spectral responsivity of the imaging sensor.

It will be appreciated that in some embodiments of the present invention, processor 12 may output the RGB data in a frame rate dependent on the spectral density, e.g. the number of different wavelength bands of illumination that should be included in the image data calculation. In some embodiments of the present invention, it is possible to adapt the frame rate by adapting the operation protocol, for example changing the number of illumination wavelength bands operated and/or included in the calculation, or improving the colors of the RBG image while providing a slower frame rate, as needed. Generally, the RGB image data is calculated by:

$$\begin{pmatrix} R \\ G \\ B \end{pmatrix} = \sum_{i=wl_1}^{wl_N} \begin{pmatrix} R_i I_i \\ G_i I_i \\ B_i I_i \end{pmatrix}$$

Wherein R, G and B are matrices representing the Red, Green and Blue image data, the $R_i$, $G_i$ and $B_i$ coefficients are the R, G, and B coefficients for illumination at wavelength I, and $I_i$ is a matrix representing the monochromatic image captured during illumination at wavelength i.

It will be noted that the present invention is not limited to generation of RGB image data and similar methods may be carried out in order to generate other color space image date, such as Hue, Saturation and Lightness (HSL); Hue, Saturation and Value (HSV), XYZ, Lab, and the like.

The system and method provided by some embodiments of the present invention, as described herein, enable acquisition of high fidelity color images with the use of narrow band illumination sources, discretely covering the effective spectrum with the imaging sensor. This method improves the image resolution, the imaging system efficiency, and enables accessibility to multi\hyper spectral data at high frame, rate without compromising the spatial resolution and without the introduction of mechanical scanning.

As indicated in block 450, in some embodiments of the present invention, processor 12 extract auxiliary information from data captured by image sensor 18 images captured by sensor 18 of light reflected from objects may be used for extraction of information besides RGB image data, such as fluorescence, auto-fluorescence, speckle patterns, structured light, and any other suitable data obtainable by spectral analysis of the reflected light. In some embodiments, information is extracted by illumination in wavelengths which are outside the human visible range (i.e. 400-680 nanometer) but are still in the sensing range of sensor 18, e.g. between 300 nm to 1150 nm.

For example, information may be extracted from coherence or other spectral properties of the sensed reflected light. The extracted information may be used for analysis of the color image, enhancement of the color image, and/or for providing additional information in parallel to the color image. For example, processor 12 may identify in the captured reflected light spectral patterns and/or properties which may be invisible and/or difficult to recognize by a human eye and/or brain and/or perception. For example, the identified spectral properties may include depth interpretation and/or estimation, which may be identified from deformation of a structured light pattern. For example, the identified spectral properties may include standard divination in speckle patterns, which may be identified in some of the captured image layers, e.g. some of the illumination bands.

The identified patterns may be displayed by an overlay on the corresponding displayed color image and/or besides the corresponding displayed color image, and/or may be used by processor 12 as additional information layers for further processing and/or classification of the color image data, and/or may be stored in the system or by any other method of digital data storage (e.g. in a cloud), as raw data or after partial processing, for future processing.

In some embodiments of the present invention, in order to acquire some kinds of spectral information, sensing module 11 may include diffractive elements and/or other form of optical lenses covering the distal end of at least some of waveguides 11a-11f. The diffractive elements and/or lenses may be configured for diffraction in pre-determined angles and/or according to pre-determined diffraction functions and/or diffraction patterns, for example according to corresponding specific spectral analysis performed on captured reflected light in the corresponding wavelengths. Thus, some embodiments provide a pre-determined diffraction structure to illumination in a specific wavelength. For example, in some embodiments, processor 12 may extract depth information about the captured image from deformation of known light pattern illuminated with over the sample with a known diversion angle relative to the image plane normal.

In some embodiments of the present invention, processor 12 may identify, resolve and/or quantify dynamics in the sensed environment, such as a moving object and/or flow of blood, by detecting and/or analyzing a speckle pattern, e.g. constrictive and destructive interference patterns in the sensed reflected light. For example, processor 12 may extract temporal changes in the standard deviation of the image intensity in speckle patterns identified in some of the captured light bands, while a coherent illumination is applied during the illumination interval.

In some cases, some illuminated objects from which captured light is reflected may undergo a process of energy transfer which changes the wavelength of the reflected light. In some cases, an object may undergo auto-fluorescence or some kind of induced fluorescence. Processor 12 may synchronize illumination and light capturing to capture an image during the illumination and an additional image with a delay between the illumination and the capturing, and may compare the immediately reflected light to the fluorescence light, thus creating an additional information layer of the change in wavelength due to fluorescence. In some embodiments, processor 12 may identify fluorescence and/or calculate the temporal response of the fluorescence, for example, by time modulation of the reflected light and according to the sensitivity of light sensor 18.

In the context of some embodiments of the present disclosure, by way of example and without limiting, terms such as 'operating' or 'executing' imply also capabilities, such as 'operable' or 'executable', respectively.

Conjugated terms such as, by way of example, 'a thing property' implies a property of the thing, unless otherwise clearly evident from the context thereof.

The terms 'processor' or 'computer', or system thereof, are used herein as ordinary context of the art, such as a general purpose processor, or a portable device such as a smart phone or a tablet computer, or a micro-processor, or a RISC processor, or a DSP, possibly comprising additional elements such as memory or communication ports. Optionally or additionally, the terms 'processor' or 'computer' or derivatives thereof denote an apparatus that is capable of carrying out a provided or an incorporated program and/or is capable of controlling and/or accessing data storage apparatus and/or other apparatus such as input and output ports. The terms 'processor' or 'computer' denote also a plurality of processors or computers connected, and/or linked and/or otherwise communicating, possibly sharing one or more other resources such as a memory and/or cloud-based storage.

The terms 'software', 'program', 'software procedure' or 'procedure' or 'software code' or 'code' or 'application' may be used interchangeably according to the context thereof, and denote one or more instructions or directives or electronic circuitry for performing a sequence of operations that generally represent an algorithm and/or other process or method. The program is stored in or on a medium such as RAM, ROM, or disk, and/or cloud storage or semiconductor based disk-like storage or any kind of RAID storage, or embedded in a circuitry accessible and executable by an apparatus such as a processor or other circuitry. The processor and program may constitute the same apparatus, at least partially, such as an array of electronic gates, such as FPGA or ASIC, designed to perform a programmed sequence of operations, optionally comprising or linked with a processor or other circuitry.

The term 'configuring' and/or 'adapting' for an objective, or a variation thereof, implies using at least a software and/or electronic circuit and/or auxiliary apparatus designed and/or implemented and/or operable or operative to achieve the objective.

A device storing and/or comprising a program and/or data constitutes an article of manufacture. Unless otherwise specified, the program and/or data are stored in or on a non-transitory medium.

In case electrical or electronic equipment is disclosed it is assumed that an appropriate power supply is used for the operation thereof.

The flowchart and block diagrams illustrate architecture, functionality or an operation of possible implementations of systems, methods and computer program products according to various embodiments of the present disclosed subject matter. In this regard, each block in the flowchart or block diagrams may represent a module, segment, or portion of program code, which comprises one or more executable instructions for implementing the specified logical function(s). It should also be noted that, in some alternative implementations, illustrated or described operations may occur in a different order or in combination or as concurrent operations instead of sequential operations to achieve the same or equivalent effect.

The corresponding structures, materials, acts, and equivalents of all means or step plus function elements in the claims below are intended to include any structure, material, or act for performing the function in combination with other claimed elements as specifically claimed. As used herein, the singular forms "a", "an" and "the" are intended to include the plural forms as well, unless the context clearly indicates otherwise. It will be further understood that the terms "comprising", "including" and/or "having" and other conjugations of these terms, when used in this specification, specify the presence of stated features, integers, steps, operations, elements, and/or components, but do not preclude the presence or addition of one or more other features, integers, steps, operations, elements, components, and/or groups thereof.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions and equivalents are not precluded.

The invention claimed is:

1. A color imaging method, the method comprising:
actively illuminating a lumen by using a plurality of predetermined series of between four and twenty independent narrow band illumination sources to carry out an illumination protocol cycle;
capturing individual narrow non-overlapping and image frames of the lumen by a monochromatic image sensor synchronously with said illuminating;
using predetermined weight coefficients representing the contribution of each of the narrow band image frames to a specific color space to generate
a corresponding high color fidelity image as a weighted sum of the different image frames using the said weight coefficients; and
displaying in real-time said high color fidelity image,
wherein each weight coefficient represents contribution of each captured individual narrow band image frame to said generated high color fidelity image, in said illumination protocol cycle.

2. The method according to claim 1, the method, further comprising:
using said individual narrow band image frames and additional frames that were captured by using illumination sources different from those of said illumination protocol cycle;
extracting information by post-processing said individual narrow band image frames and said additional frames, wherein said extracted information is additional to information used to calculate the corresponding high color fidelity image,
wherein said individual narrow band image frames and said illumination protocol cycle data are maintained together with high color fidelity image.

3. The method according to claim 1, wherein said illumination sources are, narrow band illumination sources having spectral power distribution of less than 20 nm.

4. The method according to claim 3, the method further comprising a dynamic control h a system controller over the attributes of said illumination protocol cycle according to an external command or a predefined response,
wherein said dynamic control comprises at least one, of following attributes:
(i) selecting narrow band illumination wavelengths in the protocol cycle;
(ii) changing order of illumination of said narrow band illumination sources;
(iii) controlling individual exposure times of said monochromatic image sensor frames in the illumination protocol cycle;
(iv) controlling individual intensity levels of said illumination sources; and
(v) controlling individual illumination intervals of said illumination sources,
wherein said illumination protocol cycle yields data or composition of a single-color image frame, thus the illumination protocol cycle is operated in a continuous cycle mode to perform real time high color fidelity imaging, alongside additional extracted information.

5. The method according to claim 3, using said individual narrow band frames and said additional frames that were captured by using illumination sources different from those of said illumination protocol cycle, to carry out an extraction of information by post-processing said individual narrow band image frames, while maintaining individual narrow band image frames and data of the illumination protocol cycle with a corresponding processed high color fidelity image.

6. The method according to claim 5, wherein said extracted information includes at least one of: (i) fluorescence; (ii) auto-fluorescence; (iii) flow pattern spatial distribution; (iv) flow pattern dynamics; (v) oximetry and (vi) scene depth.

7. The method according to claim 5, the method further comprising narrow band illumination frames in wavelengths outside the human visible range,
wherein said narrow band wavelengths are outside the human visible range, said illumination spectrum is within the spectral responsivity of said monochromatic image sensor.

8. The system according to claim 3, wherein the processor is configured to detect a base illumination level by controlling the illumination sources to provide no illumination during a certain interval and capturing image frame by the image sensor when no illumination is provided by the sources, the said frame determine illumination background level for: calibration, correction or real time image quality validity.

9. A color imaging system comprising:
a plurality of at least four illumination sources, each configured to provide active illumination via a waveguide in a different predetermined narrow band of wavelengths; and a processor configured to execute code, the code comprising instructions for:
individually controlling non-overlapping illumination intervals of each of the plurality of illumination sources;

controlling a monochromatic image sensor to capture a set of image frames synchronously with the illumination intervals;

receiving a set of the captured image frames; and generating in real-time high color fidelity image data from the received captured image frames.

10. The system according to claim 9, the system further comprising a sensing module said sensing module comprising:

one or more waveguides configured to transmit illumination from the different illumination sources, respectively; and a monochromatic image sensor.

11. The system according to claim 9, wherein the processor is configured to operate the illumination sources according to at least one of:

(i) a pre-programmed operation protocol of illumination;
(ii) a dynamically controlled operation protocol of illumination, wherein the processor independently controls each of the sources and the monochromatic image sensor, for at least one of: (i) used illumination source; (ii) source illumination duration; (iii) source intensity; (iv) source modulation duty cycle; (v) source modulation frequency; (vi) source modulation mode; (vii) sensor exposure duration; and (viii) sensor frame rate and wherein said modulation mode is analog or digital.

12. The method according to claim 5, wherein the illumination protocol cycle constructs of simultaneously operating at least two narrow band illuminations; or said illumination protocol cycle constructing in multiple image frames generated by illuminating in the same narrow band wavelength.

* * * * *